United States Patent [19]

Asato

[11] 4,229,383

[45] Oct. 21, 1980

[54] PROCESS FOR THE PREPARATION OF PHOSPHORAMIDATES

[75] Inventor: Goro Asato, Titusville, N.J.

[73] Assignee: American Cyanamid Company, Stamford, Conn.

[21] Appl. No.: 47,543

[22] Filed: Jun. 11, 1979

[51] Int. Cl.$^3$ .............................................. C07F 9/24
[52] U.S. Cl. ................................. 260/968; 260/926
[58] Field of Search ............ 260/926, 938 (U.S. only), 260/968

[56] References Cited

U.S. PATENT DOCUMENTS

| | | | |
|---|---|---|---|
| 3,275,502 | 9/1966 | Price et al. | 260/938 |
| 3,845,176 | 10/1974 | Weir | 260/984 |
| 4,076,809 | 2/1978 | Weir et al. | 260/926 |
| 4,086,336 | 4/1978 | Owen et al. | 260/926 |

FOREIGN PATENT DOCUMENTS

| | | | |
|---|---|---|---|
| 410009 | 5/1974 | U.S.S.R. | 260/926 |

*Primary Examiner*—Anton H. Sutto
*Attorney, Agent, or Firm*—Harry H. Kline

[57] ABSTRACT

There is provided a process for the preparation of a diphosphoramidate involving the reaction of a chlorophosphate with an alkali metal thiocyanate or ammonium thiocyanate in a water-immiscible solvent to form a cyanatidate, which is then reacted with an aqueous mixture of a phenylenediamine to yield said diphosphoramidate.

5 Claims, No Drawings

PROCESS FOR THE PREPARATION OF PHOSPHORAMIDATES

The present invention relates to a process for the preparation of diphosphoramidates. More particularly, the invention relates to a plurality of reaction steps involving, first, the reaction of a chlorophosphate with an alkali metal or ammonium thiocyanate to form a cyanatidate, and second, the reaction of the latter cyanatidate with a phenylenediamine to yield a diphosphoramidate in good yield and purity.

It is known that diethyl phosphoroisothiocyanatidate [or diethoxyphosphinyl isothiocyanate] as reported in the Canadian Journal of Chemistry, 37, 525 (1959) is susceptible to hydrolysis. Furthermore, as evidenced in U.S. Pat. Nos. 3,845,176, 4,076,809 and 4,086,336 as well as in U.S.S.R. Pat. No. 410,009 and East German Application No. 2,739,215, the reaction of the above isothiocyanate, or related isothiocyanates, with phenylenediamines in inert or aprotic organic solvents is known to afford phosphoramides. As more specifically disclosed in U.S. Pat. No. 3,845,176, patentee teaches that water should be absent from the system during reaction to prevent side reactions.

It is found that in the preparation of tetraethyl {(2-methoxy-p-phenylene)bis[imino(thiocarbonyl)]} diphosphoramidate, the recovery of 2-methoxy-p-phenylenediamine from its sulfuric acid salt is non-quantitative after neutralization. Thus, even after ten or more extractions with methylene chloride, 80% of the diamine is recoverable, while with a single extraction utilizing methylene chloride 67% of the diamine is obtained. Thus, the extraction which results in markedly lower yields is unsatisfactory. However, if the extraction step is omitted and an aqueous mixture of the neutralized diamine is employed in a subsequent reaction with a solution of diethyl phosphoroisothiocyanatidate, which is present in a suitable water-immiscible organic solvent, such as chlorinated hydrocarbons (illustrative of which are: ethylene dichloride, chloroform, or, 1,2-dichloroethane), tetraethyl-{(2-methoxy-p-phenylene)-bis[imino(thiocarbonyl)]}diphosphoramidate is unexpectedly prepared in surprisingly high yield (70–75%) and in good purity.

In general, the process of the present invention can be employed to prepare other diphosphoramidates of ortho, meta, and para phenylenediamines, which are convertible to their inorganic acid salts as well. For instance, the diphosphoramidate of 2-chloro-p-phenylenediamine, which diamine is readily available as the sulfuric acid salt, can be so prepared. Thus, the phenylenediamine acid salt is neutralized with an aqueous solution of a suitable base, as for example, sodium or potassium hydroxide, sodium or potassium carbonate (or bicarbonate), ammonium hydroxide and equivalents of the same, and the aqueous mixture of the diamine is added to a solution containing cyanatidate which is prepared in the above scheme in a water-immiscible solvent, such as ethyl acetate, butyl acetate, methyl isobutyl ketone, xylene, benzene, toluene, chloroform, methylene chloride, 1,2-dichloroethane, or carbon tetrachloride. The overall reaction reaction is then carried out at about 20° C.–40° C. under agitation. Resultant desired product is obtained by separating the organic phase and evaporating the solvent after subjecting the product to conventional filtration and drying. When the product is insoluble in the selected solvent, the product is conveniently collected by filtration and then purified further by conventional methods, such as by recrystallization from acetone.

The equations for the overall stepwise reactions according to the process hereinabove described are as follows:

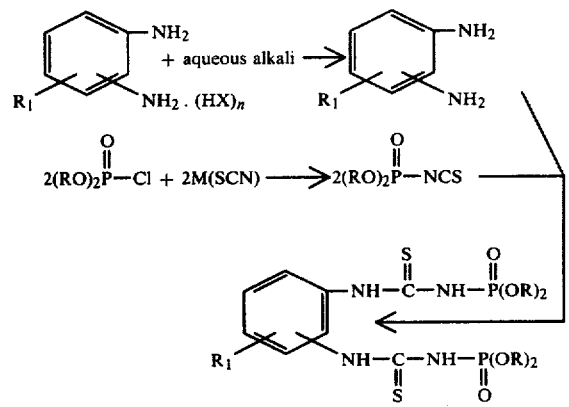

wherein n is 1 or 2, X is chloride, bromide, or $HSO_4^-$, M is sodium, potassium, ammonium, R is alkyl ($C_1$–$C_4$), $R_1$ is H, alkyl $C_1$–$C_4$, alkoxy $C_1$–$C_4$, halogen (e.g., chloride, bromine, iodine, fluorine).

In brief, the process of the present invention comprises: the steps of reacting a chlorophosphate of the formula:

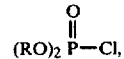

wherein R is as described above, with approximately an equimolar amount of an alkali thiocyanate, such as thiocyanate or potassium or ammonium thiocyanate, in the presence of a water-immiscible solvent, preferably at a temperature between 0° C. and 35° C. to form a cyanatidate of the formula:

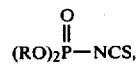

wherein R is as described above, and then reacting the so-formed cyanatidate with an aqueous mixture comprising approximately an equivalent amount of a phenylenediamine of the formula:

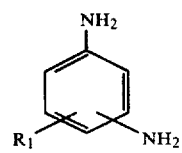

wherein $R_1$ and X are as described above, at a temperature between about 20° and 40° C., whereby the desired diphosphoramidate having the formula:

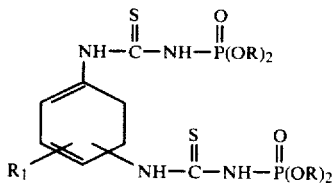

where R and R₁ are as described above.

The practice of the present invention is further illustrated by the non-limiting examples set forth below.

EXAMPLE 1

Preparation of Tetraethyl-{(2-methoxy-p-phenylene)bis[imino(thiocarbonyl)]}diphosphoramidate To a stirred mixture of 423 g (5.22 mole) of sodium thiocyanate (NaSCN) in 1.125 liters of methylene chloride ($CH_2Cl_2$) under $N_2$ is added 860.7 g (4.99 mole) of diethylphosphinyl chloride

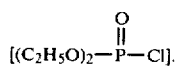

An exotherm results. It is held below 30° C. using a water bath. The mixture is then stirred at ambient temperature for 17 hours and diluted with 7 liters of $CH_2Cl_2$. In a separate reaction vessel, 179.3 g (4.48 mole) of sodium hydroxide in 3920 grams of water are added to 570.4 g (2.24 mole) of 2-methoxy-p-phenylenediamine sulfate and this mixture is stirred for an hour. Resultant mixture is then added to the $CH_2Cl_2$ solution of the corresponding isothiocyanate in 0.5 hour. An exotherm of 4° C. (24° C.–28° C.) is observed and after the addition is completed, stirring is continued for 1.5 hour. The mixture is then poured into a separatory funnel and the organic layer is separated. The remaining aqueous layer is further extracted with $CH_2Cl_2$ and the combined organic layers are dried over magnesium sulfate ($MgSO_4$) and filtered through siliceous earth. The filtrate is evaporated to dryness and the residue is stirred in acetone for 16 hours. The solid is then collected and washed well with acetone and dried to afford the title compound, m.p. 145–147 in 70–75% yields.

Utilizing the procedure of Example 1 in every detail except that diisopropyl phosphoroisothiocyanatidate is substituted for diethyl phosphoroisothiocyanatidate, tetraisopropyl {(2-methoxy-p-phenylene)-bis[imino(thiocarbonyl)]} diphosphoramidate is obtained in similar yields.

EXAMPLE 2

Preparation of Tetraethyl-{(2-chloro-p-phenylene)bis[imino(thiocarbonyl)]}diphosphoramidate Employing the process of Example 1 in every detail except that 2-chloro-p-phenylenediamine sulfate is neutralized and allowed to react with two equivalents of diethyl phosphoroisothiocyanatidate

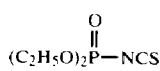

in chloroform instead of methylene chloride to afford the title compound, m.p. 148°–149° C.

Substitution of chloroform with 1,2-dichloroethane also affords the title compound in good yield.

Similarly, 4-methoxy-o-phenylenediamine hydrochloride and 4-methoxy-m-phenylenediamine sulfate trihydrate are treated in the above manner to afford tetraethyl-{4-methoxy-o and m-phenylene)bis[imino(thiocarbonyl)]}diphosphoramidate.

EXAMPLE 3

Employing the procedure of Example 1 and organic solvents utilized in the two-phase system, the following compounds are prepared. The melting points indicated are are those obtained for purified samples of the exemplified products.

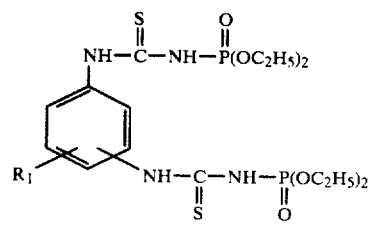

The results are tabularized in Table I below:

TABLE I

| R₁ | Solvent | Position of A | Melting Point °C. |
|---|---|---|---|
| H | $CH_2Cl_2$ | Ortho | 135.5–136.5 |
| H | $CHCl_3$ | Meta | 147–149 |
| H | $Cl—CH_2—CH_2—Cl$ | Para | 143–145 |
| 2-$CH_3$ | $CH_2Cl_2$ | Para | 156.5–157.5 |
| 4-n-$C_4H_9$ | $CH_3COOC_2H_5$ | Ortho | 60–85 |
| 4-Cl | $CH_2Cl_2$ | Ortho | 144–146 |
| 2-Br | $CH_2Cl_2$ | Para | 152–152.5 |
| 4-F | $CH_2Cl_2$ | Ortho | 148–150 |
| 2-I | $CH_2Cl_2$ | Para | 143–146 |
| 2-Cl | $CHCl_3$ | Para | 148–149 |

EXAMPLE 4

Preparation of Tetraethyl {(2-chloro-p-phenylene)bis[imino(thiocarbonyl)]}phosphoramidate To a suitable reaction vessel is added a mixture containing 1.89 g of sodium thiocyanate (NaSCN) in 10 ml of toluene is stirred in an ice bath. Next 3.8 g of

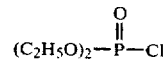

are added. Resultant mixture is then stirred for about twenty-four hours at room temperature. In a separate vessel, 2.4 g of 2-chloro-p-phenylendiamine sulfate are added to 0.84 g of sodium hydroxide in 12 ml of water. This aqueous mixture is then added to the cyanatidate solution and the resulting triphase mixture is stirred for 19 hours at room temperature. The mixture is filtered and the filter cake is collected and dried to obtain 3.3 g of the crude title compound melting at 133°–135° C. This product is further washed with acetone to yield 2.62 g melting at 142°–144° C.

Substitution of toluene with methyl isobutyl ketone in the procedure of Example 4 also yields the title compound.

I claim:

1. A method for the preparation of a phosphoroamidate having the formula:

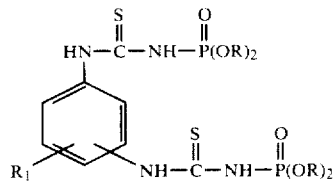

wherein R is alkyl $C_1$–$C_4$ and $R_1$ is hydrogen, alkyl $C_1$–$C_4$, halogen or alkoxy $C_1$–$C_4$, comprising: reacting a chlorophosphate of the formula:

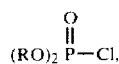

where R is alkyl $C_1$–$C_4$, with approximately an equimolar amount of an alkali metal thiocyanate or ammonium thiocyanate in the presence of a water-immiscible solvent, at a temperature between about 0° and 35° C., to form a cyanatidate of the formula:

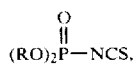

wherein R is alkyl $C_1$–$C_4$, and further reacting at a temperature ranging from about 20° C. to about 40° C. said cyanatidate with an aqueous mixture comprising approximately an equimolar amount of a phenylenediamine of the formula:

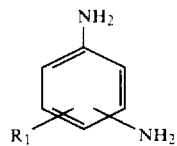

wherein $R_1$ is hydrogen, alkyl $C_1$–$C_4$, halogen or alkoxy $C_1$–$C_4$, whereby the desired phosphoroamidate is formed in good yield and purity.

2. The method according to claim 1 wherein said water-immiscible solvent is a chlorinated hydrocarbon selected from the group consisting of methylene chloride, chloroform and 1,2-dichloroethane.

3. The method according to claim 1 wherein $R_1$ is methoxy, $R_2$ is ethyl and the diphosphoroamidate is tetraethyl {(2-methoxy-p-phenylene)bis[imino(thiocarbonyl)]}di-phosphoramidate.

4. The method according to claim 1 wherein $R_1$ is chloro, R is ethyl and the diphosphoroamidate is tetraethyl {(2-chloro-p-phenylene)bis[imino(thiocarbonyl)]}diphophoramidate.

5. The process according to claim 1 for the preparation of a compound of the formula:

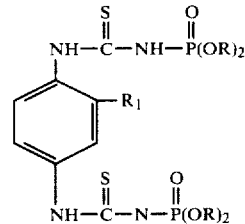

wherein R is alkyl $C_1$–$C_4$ and $R_1$ is alkyl $C_1$–$C_4$, alkoxy $C_1$–$C_4$ or halogen comprising: reacting a compound of the formula:

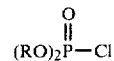

where R is as defined above, with an equivalent amount of sodium, potassium or ammonium thiocyanate, in the presence of methylene chloride, chloroform or 1,2-dichloroethane, while maintaining the temperature of the reaction mixture between about 0° and 35° C.; and treating said reaction mixture with an aqueous mixture comprising an equivalent amount of a compound of the formula;

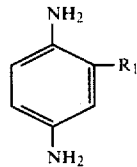

wherein $R_1$ is alkyl $C_1$–$C_4$, alkoxy $C_1$–$C_4$, or halogen while maintaining the temperature of said reaction mixture between 20° C. and 40° C., and thereafter recovering the desired product in good yield and purity.

* * * * *